United States Patent [19]

Shofner et al.

[11] Patent Number: 5,167,150

[45] Date of Patent: Dec. 1, 1992

[54] APPARATUS AND METHODS FOR TESTING TENSION-ELONGATION OR CROSS-SECTIONAL PROPERTIES OF SINGLE FIBERS AND MULTIPLE FIBER BUNDLES

[75] Inventors: Frederick M. Shofner; Youe-T Chu; Christopher K. Shofner; Mark G. Townes; Joseph C. Baldwin; David B. Patelke, all of Knoxville, Tenn.

[73] Assignee: Zellweger Uster, Inc., Knoxville, Tenn.

[21] Appl. No.: 722,604

[22] Filed: Jun. 27, 1991

Related U.S. Application Data

[63] Continuation-in-part of Ser. No. 460,292, Jan. 3, 1990, abandoned, which is a continuation-in-part of Ser. No. 293,258, Jan. 4, 1989, abandoned.

[51] Int. Cl.$^5$ .................. G01L 5/06; G01L 5/10; G01N 3/08
[52] U.S. Cl. ............................. 73/160; 73/828; 356/387; 356/429
[58] Field of Search .................. 73/159, 160, 789, 827, 73/828, 831; 356/384, 385, 387, 429; 364/560, 561, 562, 563, 564, 565; 250/559

[56] References Cited

U.S. PATENT DOCUMENTS

| | | | |
|---|---|---|---|
| 2,537,170 | 1/1951 | Steiding | 73/160 |
| 3,049,916 | 8/1962 | Weiner | 73/828 |
| 3,069,964 | 12/1962 | Simon | 356/385 |
| 3,107,523 | 10/1963 | Oliver, Jr. et al. | 73/160 |
| 3,290,932 | 12/1966 | Hitt | 73/160 |
| 4,031,746 | 6/1977 | Furuta et al. | 73/800 |
| 4,116,393 | 9/1978 | Inouye et al. | 73/160 |
| 4,173,787 | 11/1979 | Katona et al. | 73/160 |
| 4,343,637 | 8/1982 | Shofner et al. | 65/2 |
| 4,473,296 | 9/1984 | Shofner et al. | 356/336 |
| 4,511,253 | 4/1985 | Glockner et al. | 356/385 |
| 4,562,743 | 1/1986 | Bonine | 73/828 |
| 4,634,280 | 1/1987 | Paulson, Jr. | 356/385 |
| 4,885,473 | 12/1989 | Shofner et al. | 250/574 |
| 4,891,974 | 1/1990 | Wassenhoven | 73/160 |
| 4,895,028 | 1/1990 | Mayer | 73/827 |
| 5,025,660 | 6/1991 | Heusser | 73/160 |

FOREIGN PATENT DOCUMENTS

| | | | |
|---|---|---|---|
| 0226070 | 3/1958 | Australia | 73/160 |
| 0565873 | 9/1958 | Belgium | 73/160 |
| 0403988 | 12/1990 | European Pat. Off. | 73/160 |
| 0692052 | 5/1940 | Fed. Rep. of Germany | 73/160 |
| 1276934 | 9/1968 | Fed. Rep. of Germany | 73/160 |
| 0011338 | 2/1981 | Japan | 73/160 |
| 0211624 | 12/1983 | Japan | 73/160 |
| 0286326 | 8/1971 | U.S.S.R. | 73/160 |
| 0678405 | 8/1979 | U.S.S.R. | 73/160 |
| 0636567 | 5/1950 | United Kingdom | 73/160 |
| 2031960 | 4/1980 | United Kingdom | 73/160 |
| 2064106 | 10/1990 | United Kingdom . | |

OTHER PUBLICATIONS

Dorrity, J. L. et al., "A Minicomputer-controlled all-digital tensile test system," Proceedings of the IEEE, vol. 63, No. 10 (Oct. 1975).

(List continued on next page.)

*Primary Examiner*—William A. Cuchlinski, Jr.
*Assistant Examiner*—Diego F. F. Gutierrez
*Attorney, Agent, or Firm*—Luedeka, Hodges, Neely & Graham

[57] ABSTRACT

A fiber testing apparatus includes two support members for holding a fiber and a positioning mechanism to facilitate placement of the fiber into engagement with the support members. A translation apparatus moves the two support members apart while a monitor records at least one characteristic of the fiber as it is tensioned. In one embodiment, the two support members are first and second clamps and the positioning apparatus includes first and second suctions oriented to draw the fiber in opposite directions and place the fiber in a substantially linear configuration adjacent to both clamps. In another embodiment, a hook and clamp configuration is utilized, and in yet another embodiment a vacuum groove is employed to facilitate positioning of the fiber.

10 Claims, 8 Drawing Sheets

OTHER PUBLICATIONS

Research Disclosure, "Pick-up detector," No. 13710, p. 13 (Sep. 1975).

Skelton, J., "The Tensile Behavior of Fibrous Materials at High Rates of Strain and Subambient Temperatures," Materials Research and Standards, vol. 10, No. 6 (Jun. 1970).

Lord, E. and Heap, S. A., "The origin and assessment of cotton fibre maturity," International Institute for Cotton (Dec. 1988), pp. 1-38.

Sasser, Preston E., et al., "Interpretations of Single Fiber, Bundle and Yarn Tenacity Data," (Nov. 1989).

Thibodeaux, Devron, P., et al., "An Absolute Reference Method for Determination of the Maturity of Cotton Fibers," (1988).

Shofner, Frederick M., et al., "An Overview of the Advanced Fiber Information System," (Mar. 1990).

Shofner, Frederick M., et al., "Advanced Fiber Information System: A New Technology for Evaluating Cotton," (Dec. 1988).

Brochure: "Spinlab HVI 900 System," Zellweger Uster, Knoxville, Tenn. (no date).

Brochure: "ppm's Aerosol Scanner," ppm, Inc., Knoxville, Tenn. (no date).

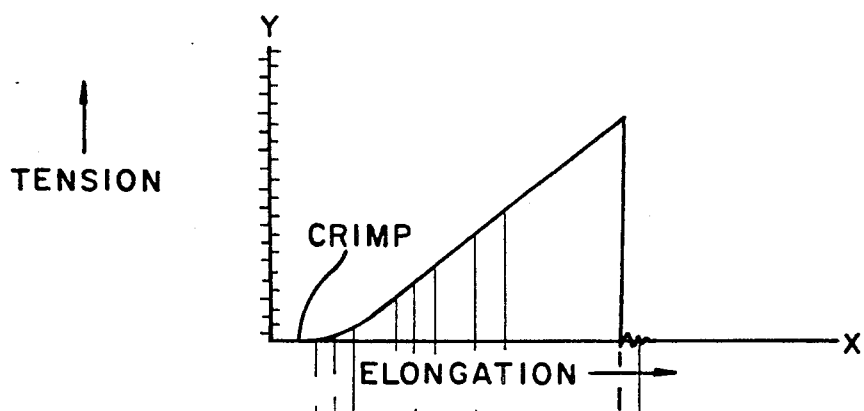
Fig. 7
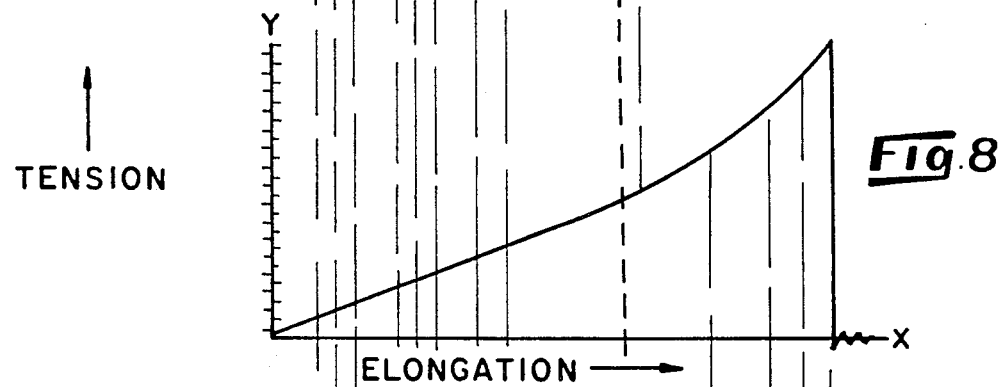
Fig. 8
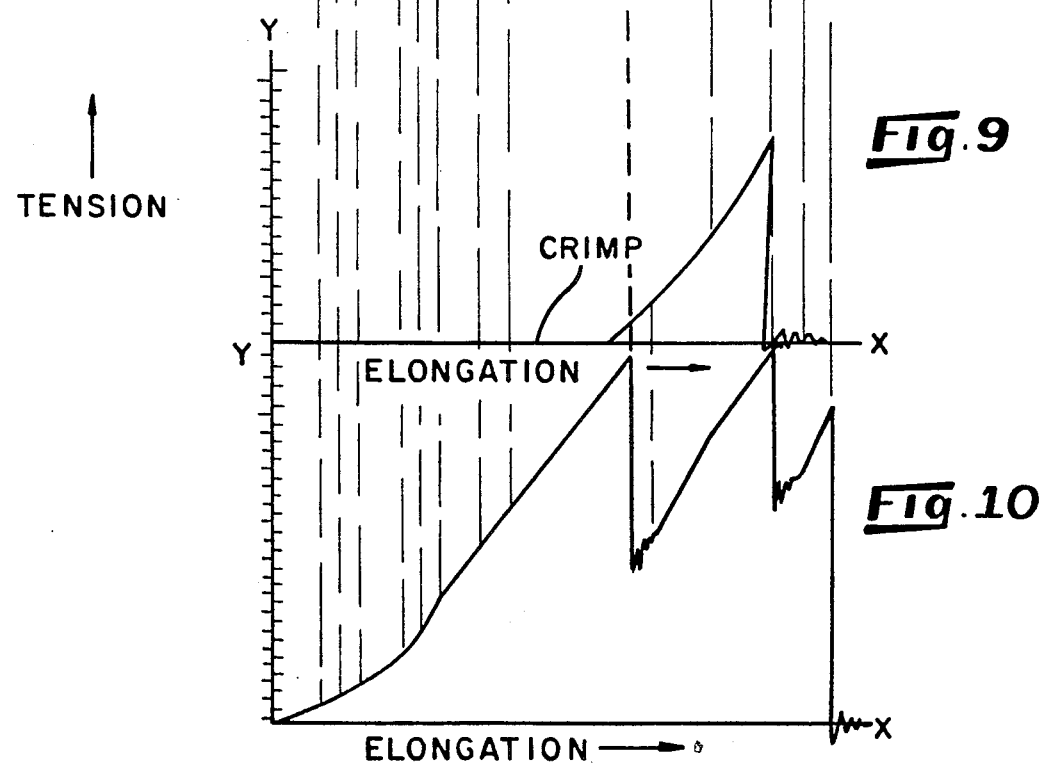
Fig. 9
Fig. 10

APPARATUS AND METHODS FOR TESTING TENSION-ELONGATION OR CROSS-SECTIONAL PROPERTIES OF SINGLE FIBERS AND MULTIPLE FIBER BUNDLES

This application is a continuation in part of application Ser. No. 460,292 filed Jan. 3, 1990, now abandoned, which is a continuation in part of application Ser. No. 293,258 filed Jan. 4, 1989, now abandoned.

FIELD OF INVENTION

This application is a continuation in part of application Ser. No. 460,292 filed Jan. 3, 1990 now abandoned, which is a continuation in part of application Ser. No. 293,258, filed Jan. 4, 1989 now abandoned, whose disclosures are incorporated. The present invention relates to fiber testing and in particular to the tensile testing of fibers for obtaining data usable in fiber manufacturing or processing.

BACKGROUND OF THE INVENTION

For proper utilization of natural or man-made fibers it is essential to have precise, accurate, and basic tensile characteristics of the fibers. To illustrate, in the making of yarn from cotton or polyester staple, in the researching of genetic influences upon characteristics of cotton or wool, or in the production of man-made fibers from carbon or glass, data relating to the tensile characteristics of the fibers commonly need to be compiled, studied, and utilized. In most basic terms, individual fibers are the building blocks, the basic materials of construction, the essence of textile yarns. It follows that their tensile characteristics are a major determinant in their proper utilization or in their preparation. Such tensile characteristics are not readily available with prior art instruments and the broadest objective of this invention is convenient and rapid provision of accurate and precise tensile data for fibers.

As used herein, the term "tensile" will be understood to include tension-elongation characteristics and cross-sectional characteristics. For example, the traditional material characteristic of tensile stress is simply the ratio of breaking force divided by cross-sectional area; common dimensions for tensile stress are pounds/inch$^2$ or newtons/m$^2$. As a second example, percentage elongation is sometimes taken as the elongation for which Hooke's Law holds (when incremental force is directly proportional to incremental elongation) divided by the untensioned length (gauge) of the material times 100%. Note that this definition of elongation is not general; it excludes elongation components when the force is small, i.e., "crimp" or "slack", or when force is not linear with elongation, i.e. plastic deformation.

It is especially desirable that such tensile data be generated conveniently and quickly and in sufficient quantities to permit the statistical analysis of the fibers' properties.

Known instruments used for obtaining tensile data from a bundle of fibers are not capable of providing data on individual fibers. In the textile industry, it is traditional to test bundles of staple fibers as opposed to single fibers. In part, the rationale behind this procedure is that fibers are normally used in bundles such as in cotton yarn (thread). However, these traditional test procedures cannot provide information about the properties of single fibers which comprise the bundle because of the impossibly complex interactions of their nonlinearities or of their distributions in peak breaking tension, elongation at break, crimp, or fiber-to-fiber friction. Even if the bundle extension rate were made extremely low and the transducer made very sensitive, so that individual fiber breaks could be observed, the exact shape of the tension-elongation diagrams of individual fibers cannot possibly be determined in general. This impossibility applies if the number of fibers in the bundle is two or more! And practical transducer responses even further preclude direct measurement of true single fiber properties from bundle tests. Even if the sensitivity of the force transducer is made very high, the data obtained from a fiber bundle test is masked by damped oscillatory response or ringing of the force transducer. That is, as individual fibers in a bundle break, a ringing oscillation is inherently set up in the test device that may distort data. Since the fibers of a bundle break at varying elongations, this ringing effect is randomly occurring throughout the majority of the test. Ringing may not significantly affect the data as to the entire bundle but it frustrates any attempt to derive precise data as to individual fiber characteristics.

Existing instruments for testing a single fiber, such as the Instron force-elongation tester, are very slow to use due to tedious manual procedures involved in preparing the fiber for testing. In that part of the textile industry using staple fibers, individual fiber testing is seldom done because the statistical quality of data thus obtained is not currently viewed as useful as bundle test data and because such single fiber tests are more expensive to acquire. For monofilament fibers, such single fiber testing is used, in spite of its expense or poor statistical basis.

Bundle tests and yarn tests, although well-established and widely used, defy rational explanation in engineering terms unless true single fiber tensile properties are known and properly and widely utilized. Yarn is, of course, a special bundle constructed of many single fibers. Absence of rational explanations of yarn properties, inhibiting advances in the fiber-to-yarn engineering process.

It is therefore, again, an objective of this invention to provide apparatus and methods for testing at least single fiber tensile properties, wherein such data are obtained conveniently, rapidly, accurately, and precisely and in sufficient quantities to be statistically meaningful. It is a further object of this invention to provide means for simulating practical bundles, including test bundles and yarn, the most practical bundle.

SUMMARY OF THE INVENTION

The present invention resides in an apparatus and methods for testing of fibers, either individually or in bundles, for the compiling of data relating to tensile characteristics of the fibers as the fibers are tensioned.

One embodiment of the apparatus for testing at least one fiber having a mid-region and two opposite ends includes a hook disposed so that the mid-region of the fiber is positionable over the hook and the fiber ends hang over opposite sides of the hook. The apparatus also includes clamp means for clamping the ends of the fiber when the fiber is positioned over the hook and translation means for moving the hook and clamp means relative to one another to tension the fiber held therebetween. Monitor means are associated with the hook and clamp means for monitoring at least one characteristic of the fiber as it is tensioned such as force-elongation, diameter, fineness, count, thickness, etc. Preferably, test zone environmental control means are provided to control the atmosphere in the immediate near vicinity of the fiber while it is being tested.

An embodiment of the method of the invention includes the steps involved in using the aforedescribed one embodiment of the apparatus. The fiber is placed so that its mid-portion is positioned across the hook and the fiber ends hang over opposite sides of the hook, and the ends of the fiber are clamped in the clamp means. The hook and clamp means are subsequently moved relative to one another to tension the fiber held therebetween, and a characteristic of the fiber is monitored as the fiber is tensioned. In the basic embodiments, force-elongation characteristics are measured.

In another embodiment of the apparatus, the apparatus includes first and second holding means for holding corresponding portions of a fiber and translation means for moving the first and second holding means relative to one another to thereby tension the fiber. The apparatus also includes electromagnetic radiation means for directing radiation onto the fiber and detector means for measuring extinction due to or the scattered radiation from the fiber. It is preferred to observe the extinction of radiation, but other angles of observation of either forward, side, or back scattering may be used. The detector means produce a signal in response to the detected radiation, and processing means in the apparatus receive the detection signal and determines a cross-sectional characteristic (such as diameter or fineness or thickness) of the fiber corresponding to the detected signal.

Another aspect of the method includes the steps involved in using the aforedescribed embodiment of the apparatus. The fiber is tensioned along its length and, at the same time, radiation is directed generally toward the fiber from one side thereof. The scattered radiation or extinction due to the fiber is detected, and a signal is produced which corresponds to the detected radiation during the time period that the fiber was under tension. A cross-sectional characteristic of the fiber is then determined in response to the produced signal.

In another embodiment of the apparatus, the apparatus includes first and second clamps, each clamp having engagement surfaces movable between a first position for clamping and holding the fiber, and a second position for releasing the fiber. A first alignment rod is positioned adjacent the first clamp for engaging and aligning the fiber with the engagement surface of the first clamp. A second alignment rod is also provided positioned adjacent to the second clamp for engaging and aligning the fiber with the engagement surfaces of the second clamp. The apparatus also includes a vacuum means for producing a suction that operates on the fiber positioned between the first and second clamps to move the fiber into position for being clamped by at least one of the clamps. Again, an electromagnetic radiation means for directing radiation onto the fiber and detector means for measuring the extinction due to the fiber or the scattered radiation from the fiber may be provided. The detector produces a detection signal in response to the detected radiation and a processing means in the apparatus receives the detect signal and determines a cross sectional characteristic of the fiber corresponding to the detection signal.

In another aspect of the method, multiple fiber data are derived from two-coordinate graphical representations (or arrays) of elongation and force characteristics of individual fibers in the bundle. Within the graphical representations, the magnitude of fiber elongation is plotted along one coordinate, and the magnitude of force exerted upon the fiber is plotted along the other coordinate. For a preselected elongation magnitude, the force values of the graphical representations are added together to obtain an additive force value, and the additive force value is plotted on a secondary two-coordinate graph wherein one coordinate of the secondary graph denotes elongation magnitudes and the other coordinate of the secondary graph denotes a range of additive force values. Force values are added together for a number of other preselected elongation magnitudes identified on the graphical representations and the resultant additive values are plotted on the secondary graph to obtain a secondary graphical representation of force-elongation characteristics for all of the fibers tested. This secondary graphical representation constitutes multiple fiber data.

Multiple fiber data obtained by the present invention is not identical to data obtained from any known bundle test, but there is correlation between multiple fiber data and both twisted fiber bundle test and parallel (brushed) fiber tests. Generally, multiple fiber data predict an upper limit for twisted bundle tests and a lower limit for parallel bundle tests. In some instances, multiple fiber data may be more useful than bundle tests. For example, if crimp is known to significantly affect performance of fibers in a certain application, then the parallel brushed bundle test would not be appropriate because crimp is uncontrollably removed (brushed out) from the fiber before the test. On the other hand, multiple fiber data normally (but not always) includes fiber crimp effects and would be more useful in predicting performance or selecting fibers from this certain applications.

In the above discussion, multiple fiber data were obtained by "adding" force values from a plurality of "graphical representations". It will be understood that "graphical representations" will normally take the form of numbers in a computer, such as a numerical array, and the term graphical representation has been chosen because it best communicates visually the invention. It does not imply that the actual production of a physical graph is necessary to the invention.

Likewise, the term "added" should be understood in a broad sense. While mathematically precise adding is preferred, the graphical representations could be combined or mixed electronically in ways that might not constitute adding in a strict mathematical sense.

BRIEF DESCRIPTION OF THE DRAWINGS

The present invention may best be understood by reference to illustrative embodiments which are shown in the accompanying drawings.

FIGS. 7-9 are graphical representations of test results carried out on individual fiber samples.

FIG. 10 is a graphical representation obtained by superimposing information borne by the graphs of FIGS. 7-9 onto a single graph.

DETAILED DESCRIPTION OF THE ILLUSTRATED EMBODIMENTS

Figure 1A:
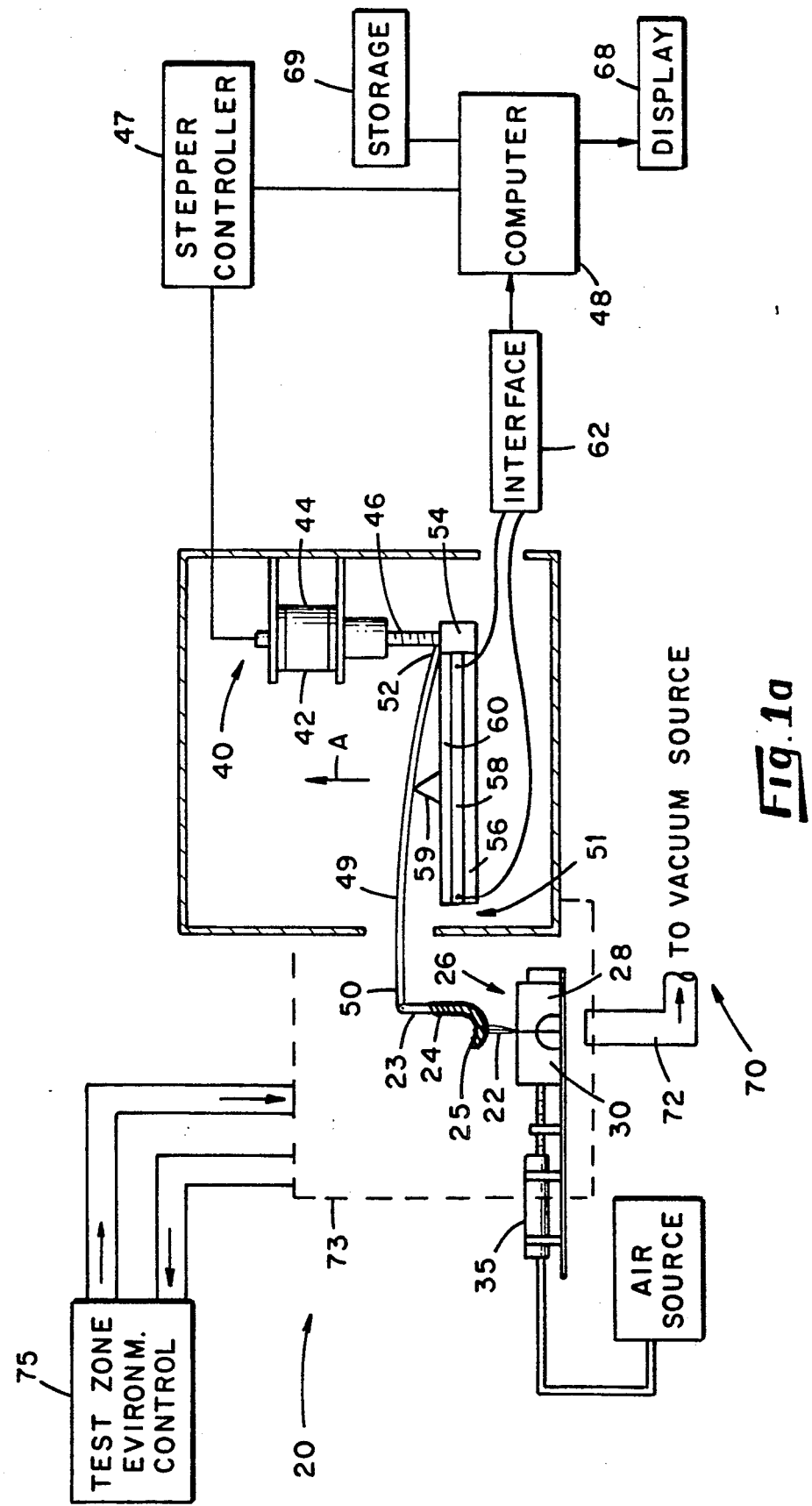
FIG. 1a is a schematic diagram of one embodiment of a fiber test apparatus.

Turning now to the drawings in greater detail, there is shown in FIG. 1 an embodiment 20 of a fiber tensile testing apparatus for performing a tensile test on a fiber 22. To perform a test with the apparatus 20, the fiber 22 is tensioned and characteristics such as the elongation of the fiber 22 and the magnitude of the tension forces placed upon the fiber 22 are monitored. Data collected on a plurality of single fibers as a result of the monitoring of such characteristics can be used to statistically analyze fibers like that of the fiber 22. While the embodiment 20 has been designed to rapidly test single fibers, it will be understood that fiber bundles may also be tested using this particular embodiment of the invention.

The apparatus 20 includes a hook 24 and clamping means, generally indicated 26, disposed in such a relationship with one another that the fiber 22 can be draped across the hook 24 and partially positioned within the clamping means 26. More specifically, the hook 24 is disposed so that the mid-portion of the fiber 22 can be positioned over the hook 24 and the ends of the fiber 22 can be clamped within the clamping means 26. The gauge, the initial or untensioned distance between the hook 24 and the clamping means 26, is preferably one eighth inch (⅛") for cotton or 1 cm for polyester staple.

Figure 1B:
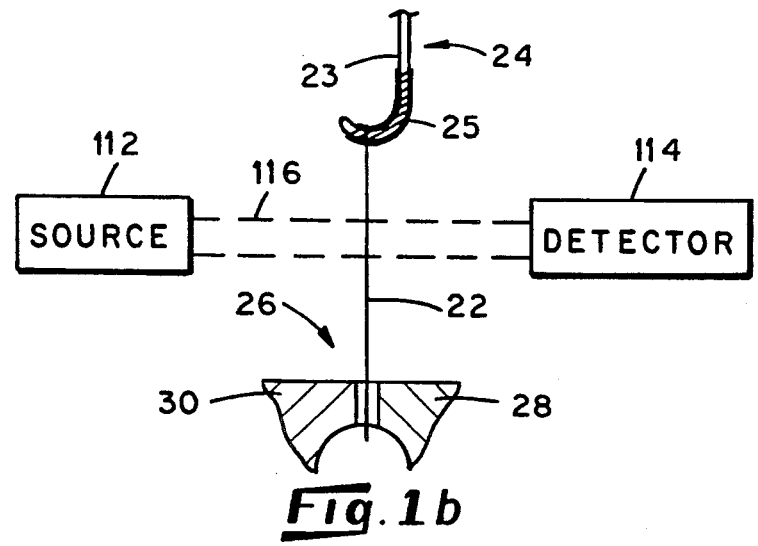
FIG. 1b is a side detail view of the hook and clamp means of FIG. 1a further showing a radiation source and detector.

The hook 24 in FIG. 1b includes a relatively rigid core 23, such as steel, and a material covering the core which provides a wear surface 25 over which the fiber 22 is draped. Preferably, the wear surface 25 is provided by a plastic material such as, for example, heat shrink tubing, to facilitate replacement of the wear surface 25 and so that frictional forces exerted upon the fiber by the hook 24 during a tensioning process are not appreciable.

Figure 2:
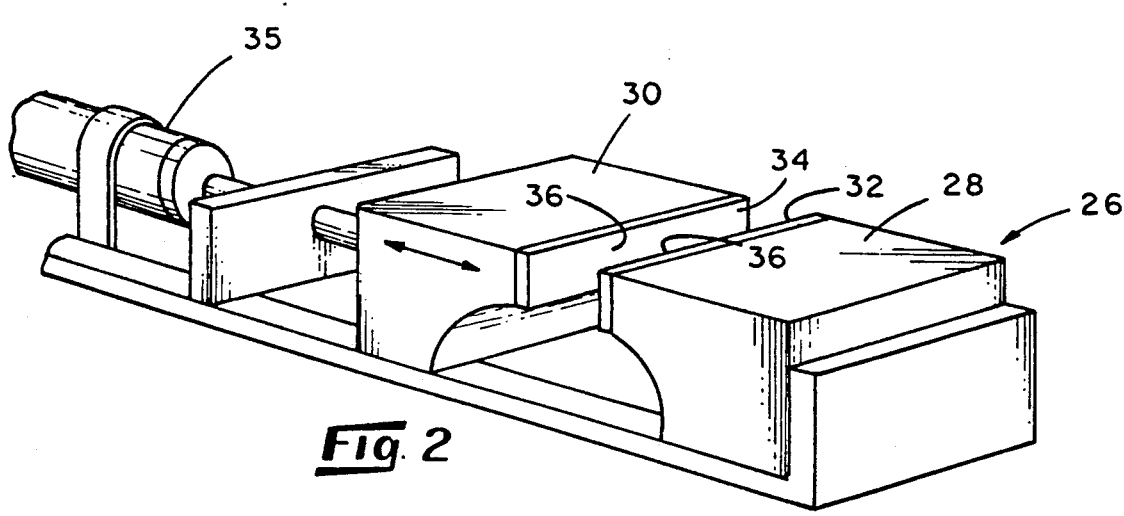
FIG. 2 is a perspective view of the clamp of the FIG. 1 apparatus drawn to a larger scale.

The clamping means 26 of the apparatus 20, best shown in FIG. 2, includes a pair of jaws 28, 30 having opposing clamping surfaces 32, 34, respectively. One jaw 28 is fixed in a stationary position and the other jaw 30 is adapted to move toward and away from the other jaw 28 in response to appropriate actuation of an air cylinder 35 so that the clamping surfaces 32, 34 move into and out of contact with one another. To prevent the fiber 22 from being cut or deformed by the clamping surfaces 32, 34 of the jaws 28, 30 each surface 32 or 34 is covered with a relatively nonresilient lining material 36, such as paper or suitable plastic. When the fiber 22 is clamped between the surfaces 32, 34 the lining material 36 prevents the fiber 22 from slipping and adds no extraneous forces to the fiber 22.

With reference again to FIG. 1a, the apparatus 20 includes translational means, generally indicated at 40, for moving the hook 24 and clamping means 26 relative to one another so that the fiber 22 connected therebetween is placed under tension. In the depicted embodiment 20, the translational means 40 includes a reversible stepping motor 42 having a housing 44 which is mounted in a stationary condition and a threaded shaft 46 which is mounted within the housing 44 for lengthwise movement relative thereto when the motor 42 is energized. Actuation of the motor 42 is controlled by a controller 47 which is controlled by computer 48 so that when desired, the shaft 46 is rotated and platform 51 is moved upwardly or downwardly, as viewed in FIG. 1, upon appropriate actuation of the motor 42. There is interposed between the hook 24 and the lower end of the shaft 46 an elongated connecting truss member 49 having two ends 50, 52 joining the hook 24 and platform 51. Fixed end 52 is held by an anchor member 54. A transducer 58 is mounted between a lower plate member 56 and an upper plate member 60 of the platform 51. An actuator 59 is disposed below the truss member 49 so that forces on the hook 24 are transmitted to the transducer 58 through the actuator 59. The actuator 59 is free to compress the transducer 58 as the connecting truss member 49 is urged downwardly. The transducer 58 includes a strain sensitive material, such as a piezoelectric crystal, which is sensitive to the compression applied by the actuator 59.

To tension the fiber 22 with the apparatus 20, the fiber 22 is positioned over the hook 24 so that the ends of the fiber 22 hang on opposite sides of the hook 24. These free ends are drawn between open jaws 28, 30 by suction means 72, described below. The ends of the fiber 22 are then clamped between the jaws 28, 30 of the clamping means 26 when they move to the closed position. At this starting point, the gauge, the distance between the hook 24 and the clamp means 26, is about one eighth inch (⅛"). The stepping motor 42 is subsequently actuated to rotate the shaft 46 and platform 51 is raised in the direction of the arrow A (FIG. 1). As the platform 51 is raised, the fiber 22 resists upward movement of the hook 24 so that the fiber 22 is exposed to tension forces and so that the actuator 59 is urged downward, in opposite direction to arrow A. The transducer 58 is consequently compressed so that a voltage measurement taken across the transducer 58 corresponds to the magnitude of compression to which the transducer 56 is exposed. The transducer 58 is appropriately connected to a an electronic interface 62 so that the voltage measurement taken across the transducer 58 at a predetermined instant of time corresponds proportionally to the magnitude of compression force on the transducer 58, and thus to the magnitude of the tension force applied to the fiber 22. For recording the voltage measurements taken across the transducer 58 as a function of time and for later analysis and display of such measurements, the electronic interface 62 is appropriately connected to the computer 48, which normally includes display means 68 and storage means 69.

For purposes of monitoring the elongation of the fiber 22 during a testing operation, the computer 48 which is responsible for the actuation of the motor 42 monitors the lengthwise displacement of the platform 58 with respect to time during a testing operation. This monitoring is preferably accomplished by monitoring and controlling the incremental steps of stepping motor 42, but other conventional length measuring techniques could be employed. By monitoring and controlling the motor 42, the computer 48 is able to monitor the corresponding elongation of the fiber 22 with respect to time. As is apparent herein, tensile force data collected on an individual fiber by way of the electronic interface 62 and displacement data of the platform 58 can be plotted to form two-coordinate graphical representations similar to those shown in FIGS. 7–9. It is preferred to monitor and record fiber tension forces as a function of time and fiber elongation lengths as a function of time. By causing the elongation of the fiber to be constant (linear) with respect to time, fiber elongation and time are linearly related and time can easily be converted to elongation by applying an appropriate linear function. The object is to produce a table or array of values in computer 48 containing a tension force value for each of a plurality of elongation values. Graphically, this table of values may be represented by a plot of tension force on one axis and elongation length on another axis.

With reference again to FIG. 1, the apparatus 20 also includes vacuum means 70 for drawing the ends of the fiber 22 between the jaws 28, 30 of the clamping means 26 when in the open position when preparing the apparatus 20 for testing. More specifically, as the fiber 22 is manually draped across the hook 24 and the jaws 28, 30 are spaced apart, the opposite ends of the fiber 22 are drawn between the open jaws 28, 30 by the vacuum means 70. To this end, the vacuum means 70 includes a conduit 72 appropriately connected to a vacuum source and directed generally toward the hook 24 so as to draw air between the jaws 28, 30 when they are open. With the use of the vacuum means 70, a fiber sample can be properly placed upon the hook 24 rapidly and with relative ease. Thus, the vacuum means 70 reduces the time which would otherwise be required to prepare the apparatus 20 for testing and is ergonomically advantageous in this respect.

With reference again to FIG. 1, the testing apparatus 20 may be calibrated by hanging a variety of known weights on the hook 24 and recording within the computer 48 the corresponding voltages produced across the transducer 58. With information regarding the weights and the corresponding voltages measured across the transducer 58, the computer 48 can calculate during a tensioning test the amount of tension exerted upon a fiber as a function of the measured transducer voltage.

It is preferred that the environment of the area within which a fiber test is performed be precisely controlled in order to provide consistent test results. To this end a microenvironment 73 is formed around the fiber during testing. The atmosphere within the microenvironment is controlled by a test zone control system 75 that pumps a desired atmosphere, such as humid air, into the microenvironment and withdraws atmosphere from the microenvironment 73. The control system 75 monitors the atmosphere using sensors (not shown) that are placed either inside the microenvironment 73 or that are disposed to monitor the withdrawn atmosphere. The microenvironment 73 is formed preferably of transparent material such as plexiglass or vinyl and provides an opening for access to the fiber 22. The control system 75 continuously floods the microenvironment with the desired atmosphere so that leakage, even massive leakage, is permitted. In the field of processing fibers, systems have been developed to control the environment in which fibers are processed and one such system is shown in U.S. Pat. No. 4,631,781, entitled Condition Gas Flow Methods for Processing and Cleaning Fiber, Separation. An aspect of the present invention is to provide a similar environmental control in a test zone or microenvironment of a fiber testing apparatus such as shown in FIG. 1.

Figure 1C:
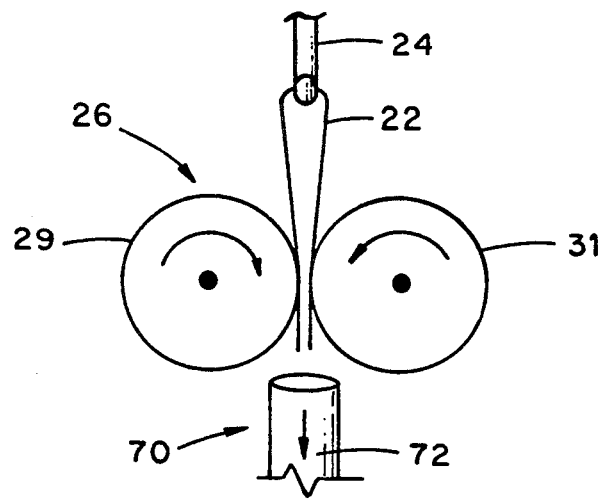
FIG. 1c is a detail view of the hook of FIG. 1a shown with a clamp in the form of rotating opposed rollers.

While the above embodiment has been described in terms of a moving hook 24 and stationary clamp means 26, it will be understood that relative movement between the two is the essential requirement, but either or both could be moving. FIG. 1c shows an alternate embodiment in which the hook 24 is stationary (at least while the fiber 22 is being broken) while the clamp means 27 moves in a rotational motion. The clamp means 27 includes two rollers 29 and 31 that are opposed, in contact, and rotate in opposite directions. A fiber 22 is positioned over the hook 24 and both are (or may be) moved into position over the rollers 29 and 31. Vacuum means 70 provided by conduit 72 draws the fiber 22 generally towards the rotating rollers 29 and 31 and, as the rollers rotate, they grip and pull the fiber 22 downwardly, elongate the fiber, place a tension on the fiber, and eventually break it. As before, elongation of the fiber corresponds to time because the rollers 29 and 31 move with constant rotational velocity. In this use the clamp means 26 provides translation of the fiber by rotational movement, but a linear movement of a clamp means could likewise provide the linear pull or translation of the fiber 22.

Figure 1D:
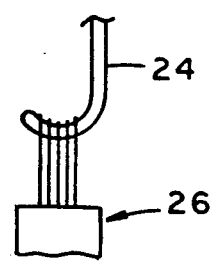
FIGS. 1d and 1e show detailed views of the hook and clamp of FIG. 1 with a parallel fiber bundle shown in FIG. 1d and a twisted bundle shown in FIG. 1e.
Figure 1E:
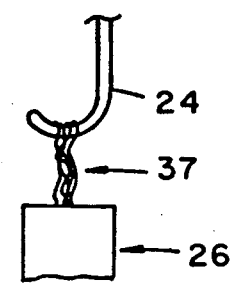

Although the embodiment of FIG. 1a is intended primarily for single fiber testing, it could be used to test multiple fibers. For example, FIG. 1d shows multiple parallel fibers 37 mounted over the hook 24 and clamped in clamp means 26 in position for break testing, and FIG. 1e shows a twisted bundle of fibers 37 similarly mounted. It can be appreciated that the test configuration of FIG. 1e simulates staple yarn, which derives its primary strength from fiber-to-fiber friction imparted by twist.

Figure 3:
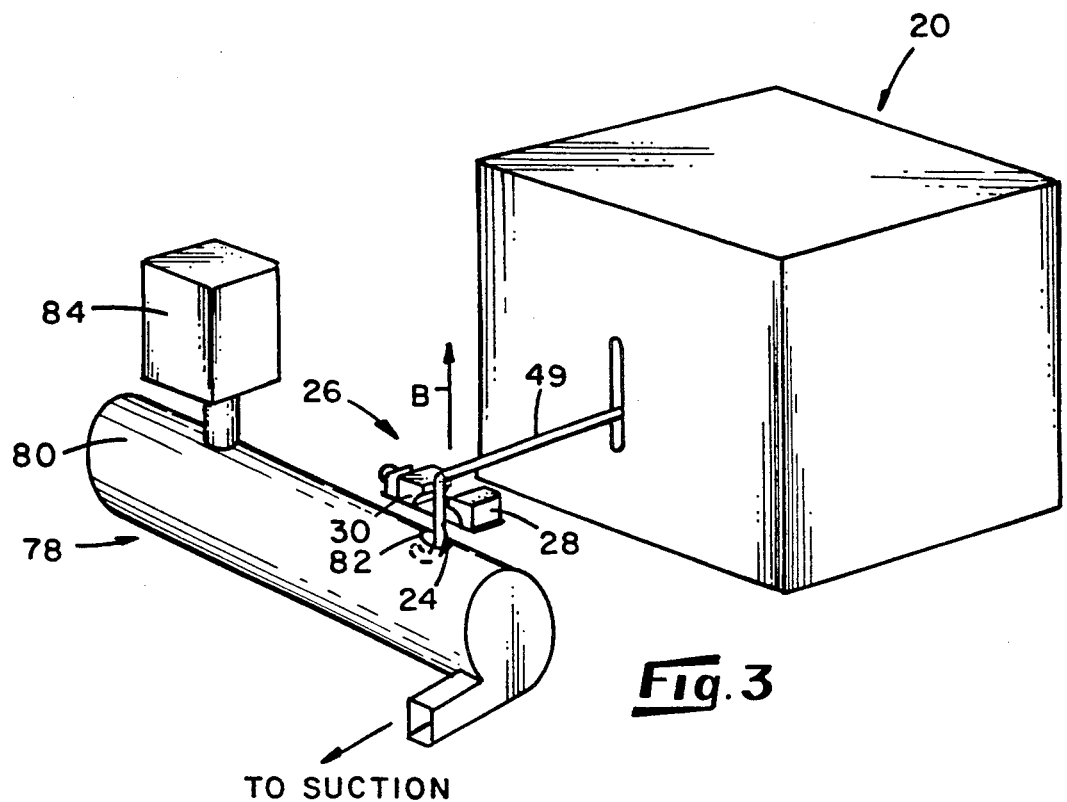
FIG. 3 is a perspective view of the FIG. 1 apparatus when used in conjunction with an automatic fiber delivery system and illustrating the condition of the apparatus when its hook is positioned in a condition for receiving a fiber delivered from the fiber delivery system.
Figure 4:
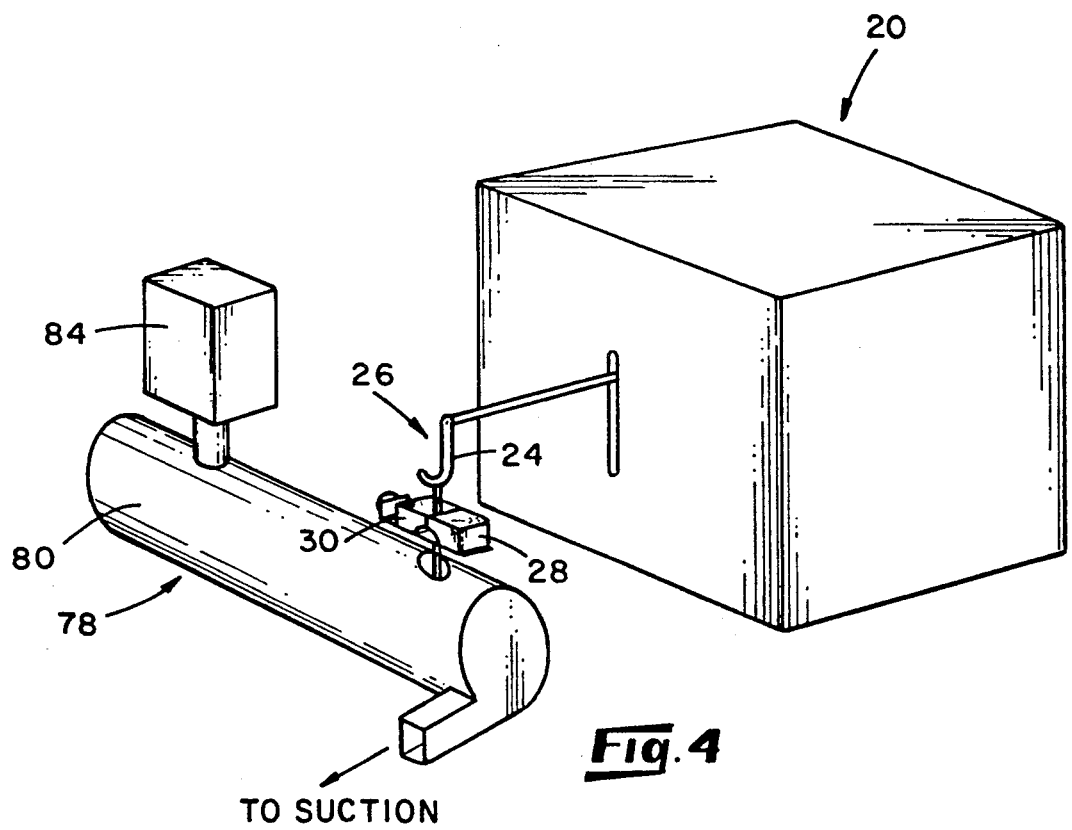
FIG. 4 is a view similar to that of FIG. 3 illustrating the condition of the apparatus when its hook is positioned in a condition for testing a fiber draped across the hook.

With reference to FIGS. 3 and 4, the FIG. 1 apparatus 20 is shown utilized in conjunction with a system, generally indicated 78 for automatically positioning a fiber (or a fiber bundle) upon the hook 24 for a testing operation. The system 78 includes an air conduit 80 having an opening 82 through which the hook 24 is lowered and raised by means of the stepping motor 42 (FIG. 1). The system 78 also includes a fiber preparation and separation device 84 for introducing a fiber into the conduit 80, and means associated with the conduit 80, such as a vacuum source and baffles (not shown), for inducing a flow of air from one conduit end to the other conduit end along a generally helical path.

When the hook 24 is in its lowered condition through the conduit opening 82 as illustrated in FIG. 3, the hook 24 is in a position for hooking a fiber moving through the conduit 80. Therefore, a fiber which is introduced into the conduit 80 and moved therethrough by the conduit airflow is caught by the hook so that the opposite ends of the fiber are draped thereacross. Once the fiber is caught, or hooked, as aforedescribed, the hook 24 is raised in the direction of the arrow B (FIG. 3) to the FIG. 4 raised condition so that the ends of the fiber are positioned between the open jaws 28, 30 of the clamping means 26. At that point, the fiber ends are clamped within the clamping means 26, and a tensile test may be performed on the fiber with the apparatus 20. By utilizing the system 78 to automatically deliver single fibers or a bundle of fibers to the hook 24 for testing purposes, a series of fiber tests may be completed at a relatively fast rate.

Figure 5:
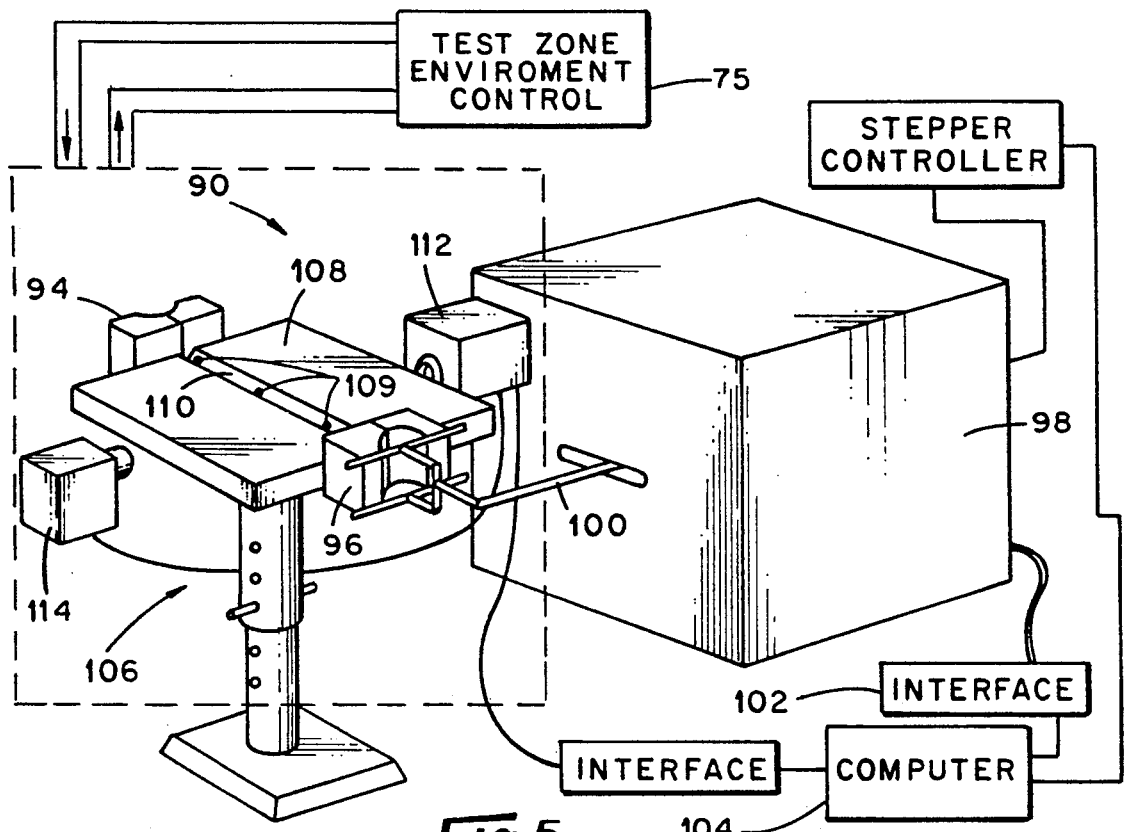
FIG. 5 is a schematic diagram of an alternative embodiment of a fiber test apparatus illustrating the relationship of various apparatus components in preparation of a testing operation.
Figure 6:
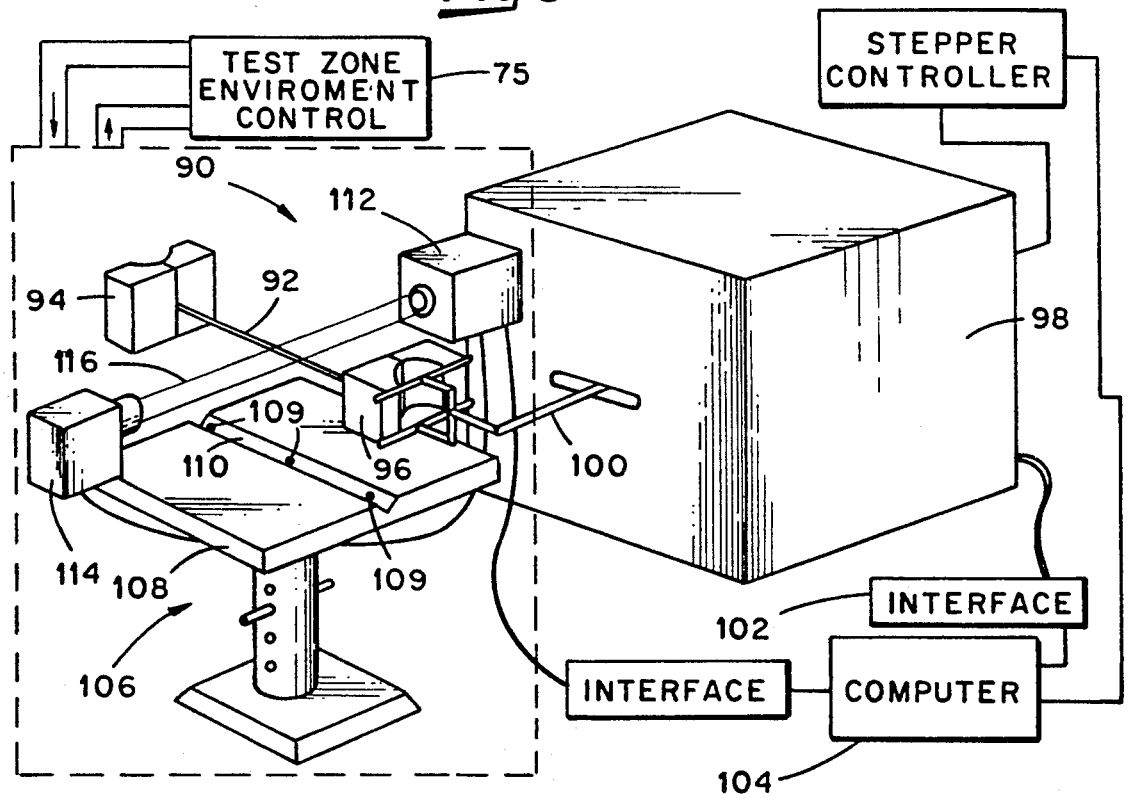
FIG. 6 is a view similar to that of FIG. 5 illustrating the relationship of various apparatus components during the course of a testing operation.
Figure 11:
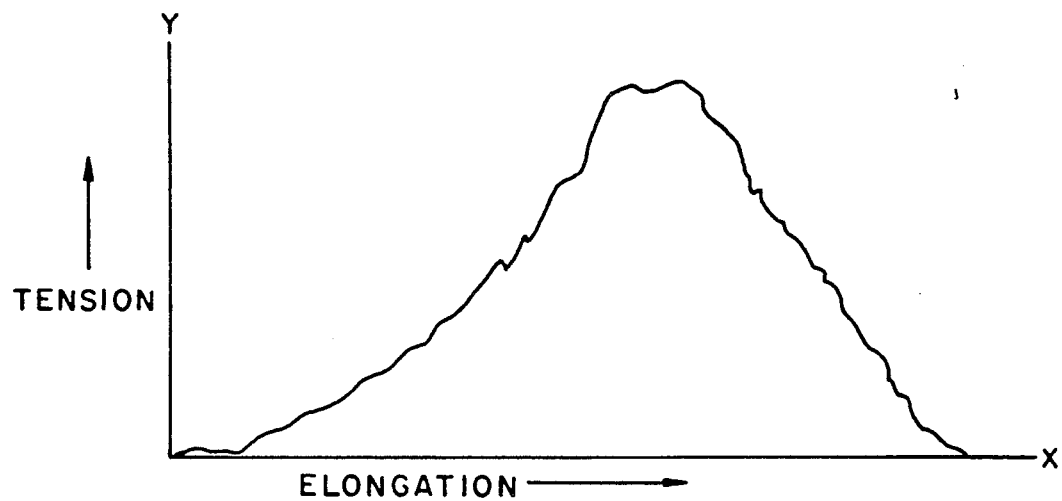
FIG. 11 is a graphical representation obtained by superimposing information borne by a large number of graphs like those of FIGS. 7-9 onto a single graph.

Referring to FIGS. 5 and 6, there is illustrated an alternative embodiment 90 of an apparatus for performing tensile tests on a fiber 92. The apparatus 90 includes two clamps 94, 96 arranged so that each end of the fiber 92 can be clamped within a corresponding clamp 94 or 96. One clamp 94 is mounted in a stationary condition, while the other clamp 96 is associated with a tensioning device 98 whose principles of operation are like those of the apparatus 20 of FIG. 1. It will be understood that the clamp 96 is shown diagrammatically in FIGS. 5 and 6, and in actual practice the clamp 96 will be constructed with a minimum of mass and a maximum of clamping to minimize ringing and other mass related effects. The tensioning device 98 includes a stepping motor (not shown) which is connected to the clamp 96 by means of a connecting member 100 so that by appropriate actuation of the stepping motor of the device 98, the clamp 96 can be moved away from the clamp 94 to tension the fiber 92 secured therebetween. Alternately, the clamp 94 may be moved away from clamp 96. A tension or force transducer such as a piezoelectric transducer (not shown) interposed between the connecting member 100 and the stepping motor of the device 98 for sensing compression as the fiber 92 is tensioned and produces a voltage corresponding to the sensed compression. The transducer of the device 98 is appropriately wired to a an electronic interface 102 and computer 104 for measuring the transducer voltage and determining the corresponding tension force. The tensioning device 98, in conjunction with computer 104 and interface 102, monitors and measures tension force and elongation of the fiber in substantially the same manner as the embodiment of FIG. 1.

To facilitate the precise positioning of the fiber 92 between the clamps 94, 96 there is provided a table mechanism 106 having a platform 108 capable of movement between a raised position, as shown in FIG. 5, and a lowered position, as shown in FIG. 6. The platform 108 defines a linear V-shaped, groove 110 in its upper surface so that when positioned in the FIG. 5 raised position, the groove 110 extends between the clamps 94 and 96. When moved to its lowered FIG. 6 position, the platform 108 is removed from the vicinity of the clamps 94 and 96 and situated in an out-of-the-way condition. Air suction holes 109 are provided in the bottom of the V-shaped groove 110 to further facilitate loading of a fiber into the groove 110.

To position a fiber 92 between the clamps 94, 96 the fiber 92 is placed within the groove 110 of the platform 108 so that its ends overhang opposite edges of the platform. The platform 108 is then raised to the FIG. 5 raised position between the clamps 94, 96 and each end of the fiber 92 is clamped within a corresponding clamp 94 or 96. During the period of time that the fiber 92 is being clamped within the clamps 94, 96 the groove 110 maintains the fiber 92 in a linear condition. Once the fiber 92 is clamped as aforedescribed, the platform 108 is lowered to the FIG. 6 position. The tensioning device 98 then moves the clamps 94, 96 relative to one another to initiate a testing operation. As was previously described with respect to FIG. 1, the fiber test is carried out within a temperature and humidity controlled environment provided by test zone environmental control 75.

The apparatus 90 further includes a source 112 of electromagnetic radiation, such as an infrared light emitting diode, supported to one side of the clamps 94, 96 and a detector 114, such as an infrared detector, supported to one side of the clamps 94, 96 opposite the light source 112. The light source 112 and detector 114 are arranged in such a relationship to the fiber 92 extending between the clamps 96, 98 so that at least a portion of a light beam 116 (FIG. 6) directed by the light source 112 toward the detector 114 interacts with the fiber, that is, is scattered or absorbed by the fiber 92. The light source 112 and detector 114 are appropriately connected to the computer 104 and to one another so that information regarding the amount of the light beam 116 scattered or absorbed by the fiber 92 is sent by the detector 114 to the computer 104. By comparing the amount of light detected by the detector 114 when the fiber is positioned in the beam 116 to the amount of light detected by the detector 114 when the fiber is not positioned in the beam 116, the computer 104 can determine characteristics relating to the cross section of the fiber 92. Such characteristics may include, for example, the diameter of the fiber cross section. For purposes of comparing the amount of light detected by the detector 114 to known values, the computer 104 has been preprogrammed with cross sectional information relating to several calibration fibers with known diameters and the corresponding amounts of light which are sensed by the detector when those fibers are positioned within the light beam. Although FIG. 6 shows an embodiment in which the detector responds to extinction, other detector positions would also work. For example, one may wish to monitor forward scattered light ($\approx 45°$) or measure the amount of light backscattered ($\approx 180°$) by the fiber depending in a particular application. As used herein, the term scattered light will be used in a broad sense and is intended to include back, side and forward scattering.

The light source 112 and detector 114 thus provide means by which cross sectional characteristics of a fiber may be monitored as the fiber is being tensioned with the tensioning device 98. Therefore, multivariate data consisting of force, elongation and cross-sectional information can be gathered by the computer 104 for a single fiber in a single testing operation. It will be understood that the light source 112 and detector 114 may also be used with the apparatus 20 of FIG. 1 to determine cross-sectional information as a test with the apparatus 20 is performed. This variation is shown in FIG. 1b.

Figure 12:
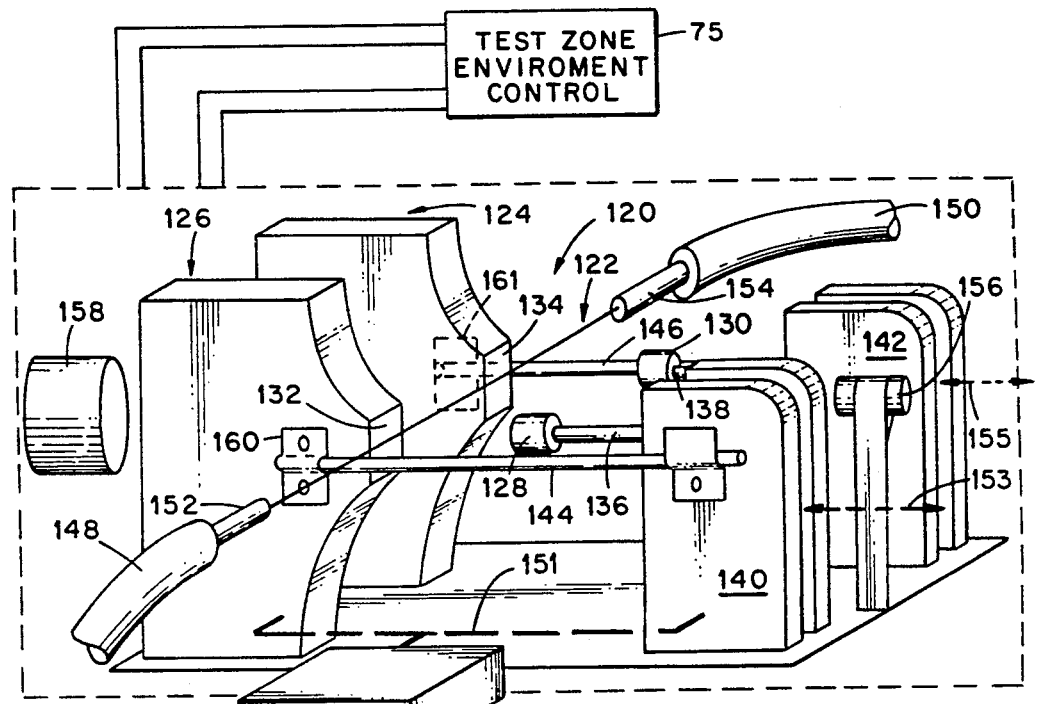
FIGS. 12 and 13 are perspective views of an alternative embodiment of the invention.
Figure 13:
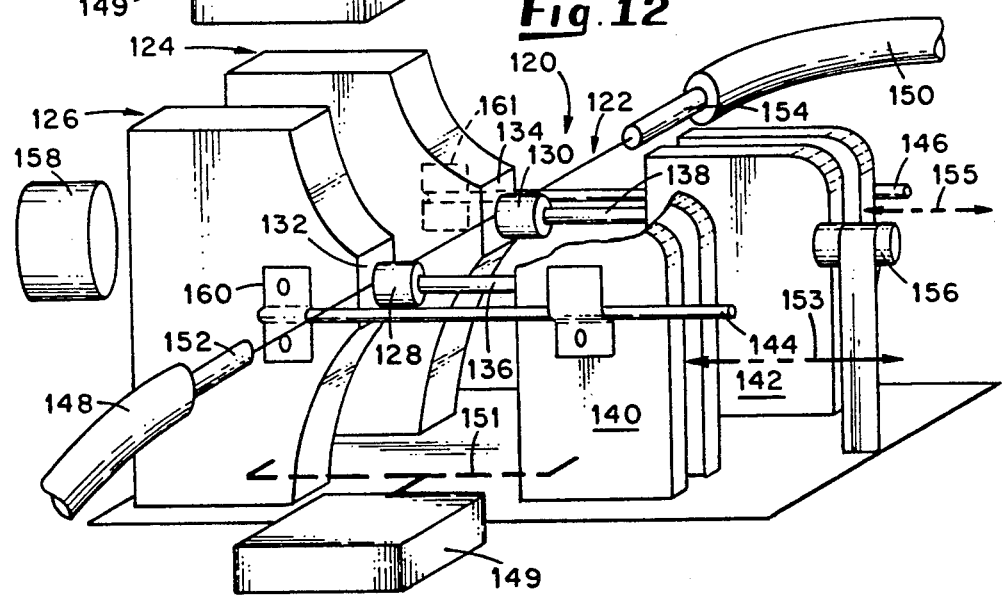

Yet another embodiment 120 of an apparatus for performing tensile tests on a fiber 122 (it should be understood that fiber 122 represents a single fiber or a single bundle of fibers) is shown in FIGS. 12 and 13. The apparatus 120 includes two clamps 124 and 126 arranged such that the fiber 122 can be clamped with clamps 124 and 126. Each clamp 124 and 126 has a clamping pad 128 and 130 which engages a clamping base 132 and 134 to clamp the fiber 122 in position to perform the tensile test. The clamping pads 128 and 130 are attached to clamping arms 136 and 138. These clamping arms 136 and 138 are mounted to clamp plates 140 and 142.

Alignment rods 144 and 146 are provided to position the fiber 122 against the clamps' bases 132 and 134 to clamp the fiber 122 in position. Each rod 144 and 146 has a first and second end with the first end mounted to the clamps 124 and 126 adjacent the clamp bases 132 and 134 with mount plates 160 and 161. Each second end of the rods 144 and 146 is slidably mounted to the clamp plates 140 and 142 thereby allowing the alignment rods 144 and 146 to maintain their horizontal position when the clamp plates 140 and 142 clamp the fiber 122.

The apparatus 120 further includes suction tubes 148 and 150 having nozzles 152 and 154 attached to one end of the suction tubes 148 and 150. These suction tubes 148 and 150 with nozzles 154 and 152 facilitate in the precision positioning of the fiber 122 in the clamps 124 and 126 and work in concert with the alignment rods 144 and 146. To position the fiber 122 in the clamps 124 and 126, the fiber 122 is placed across the alignment rods 144 and 146. The vacuum from the vacuum tubes 148 and 150 orients the fiber 122 in the proper horizontal position in front of the clamp bases 132 and 134. Once the fiber 122 is in the alignment position between both suction tubes 148 and 150 and on the alignment rods 144 and 146, one of the clamping plates 140 or 142 is moved toward the clamping bases 132 or 134 thereby forcing a clamping pad 128 or 130 against the fiber 122 and the clamping base 132 or 134. Following the first clamping of the fiber 122 by one of clamp pads 128 or 130, the other clamping pad 130 or 128 clamps the fiber 122 against clamp base 134 or 132. The characteristics of the fiber 122 are then measured to determine its characteristics at a normal untensioned or slightly-tensioned state. A slight tension removes crimp or slack. Once the cross-sectional characteristics of the fiber 122 are measured, then one clamp, either 124 or 126, is released and moved closer to the other clamp either 126 or 124, and reclamped. The suction from vacuum tube 148 or 150 and alignment rod 144 or 146 maintains the fiber 122 in its position while the clamp 124 or 126 is being repositioned. Once clamp 124 or 126 is repositioned and reclamped, tension is applied to the fiber 122 by movement of clamps 124 and 126 away from each other. The characteristics of fiber 122 are measured throughout the tensioning of the fiber 122 until the fiber 122 breaks. The movement of the clamps 124 and 126 and the measurement of the tension on fiber 122 is accomplished by fiber tensioning device 149. Tensioning device 149 and dashed lines 151 are a schematic representation of a conventional translation and measuring mechanism for moving clamps 126 (including clamp plate 140) relative to clamp 124 and clamp plate 142 and for measuring the tension on the fiber 122 (FIG. 12) as the clamps 124 are moved apart. Dashed arrows 153 and 155 represent conventional means for moving the clamp plates 140 and 142 between the positions shown in FIGS. 12 and 13 to thereby open and close clamps 126 and 124.

The apparatus 120 further includes a source 156 of electromagnetic radiation, such as an infrared light emitting diode, supported externally or in between clamping plates 140 and 142 and a detector 158, such as an infrared detector, supported externally or between the clamping bases 132 and 134, generally opposite the light source 156. The light source 156 and detector 158 are arranged such that the fiber 122 extending between the clamps 124 and 126 will interact with the light beam from light source 156 such that the light is scattered and absorbed by the fiber 122. The detector 158 will then detect this absorption or scattering of light and produce detection signals. Each detection signal is sent back to a computer (as in FIGS. 5 and 6) to determine the characteristics relating to the cross section of the fiber 22. As stated above such characteristics may include, for example the diameter of the fiber cross section. Again, for purposes of comparing the amount of light detected by the detector 158 to known values, the computer has been preprogrammed with cross sectional information relating to several calibration fibers with known diameters and the corresponding amounts of light which are sensed by the detector when those fibers are positioned within the light beam from the light source 156. As referenced above, other embodiments of the detector and positioning of the detector may also be implemented, for example one may wish to monitor the forward scattered light or measure the amount of back scattered light. As was previously described with respect to FIGS. 1, 5, and 6, the measurement of the fiber in accordance with FIG. 12 is carried out in a test zone having environmental controls of humidity and temperature which are regulated by test zone environment control 75.

Figure 14:
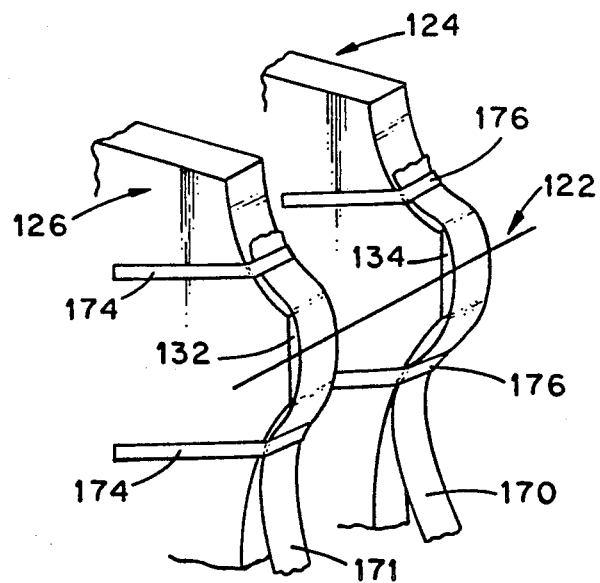
FIG. 14 is a detailed view of the clamp bases of the alternative embodiment.

FIG. 14 shows a detailed perspective view of the clamp bases 132 and 134 shown with lining material 170 and 171. The lining material 170 and 171 is now shown in FIGS. 12 and 13 in order to maintain FIGS. 12 and 13 clear and understandable. The lining material 170 and 171 is preferably paper when testing cotton or carbon fibers and soft metal for ceramic fibers, for examples. The use of the lining material 170 and 171 prevents the fiber 122 from slipping and adds no extraneous force to the fiber 122 when the fiber 122 is clamped and tensioned. Clips 174 and 176 attach to clamps 124 and 126 and maintain the lining material 170 and 171 in position adjacent to clamp bases 132 and 134.

With reference to FIGS. 7-9, there are shown two-coordinate graphical representations of elongation and tension data collected when subjecting three fibers to a tensile test with the apparatus 20 of FIG. 1 or with the other embodiments herein disclosed. More specifically, FIG. 7 is a graphical representation of the test results gathered when tensioning a first fiber until it breaks; FIG. 8 is a graphical representation of the test results gathered when tensioning a second fiber until it breaks; and FIG. 9 is a graphical representation of the test results gathered when tensioning a third fiber until it breaks. In each graph of FIGS. 7-9, the magnitude of the fiber elongation is plotted along the abscissa (x), and the corresponding magnitude of the tensile forces is plotted along the ordinate (y).

In the computer 48 of FIG. 1 or 104 FIG. 5, the force-elongation readings are stored in ordered arrays corresponding to ordered pairs (x,y) on each of FIGS. 7-9. The locus of all such ordered pairs is simply the force-elongation graph. Since equal x-values correspond to identical values of elongation, and since elongation is directly proportional to time, the same x-value corresponds to alignment in time; thus the graphs of FIGS. 7-9 can be called "time-aligned arrays".

That is, for emphasis, time-aligned force-elongation arrays can be manipulated to model the total force on the hook for a multiplicity of fibers. This will now be explained using the graphical representations of FIGS. 7-9.

In order to predict the tensile characteristics of a bundle of fibers comprised of the three fibers whose test results are graphically illustrated in FIGS. 7-9, the graphical representations of FIGS. 7-9 may be superposed on one another to form the graph of FIG. 10. To superpose the graphs of FIGS. 7-9, the tensile stress values of the graphical representations for a preselected elongation magnitude are added together to obtain one additive stress value, and the additive stress value is plotted on a secondary graph (i.e., the graph of FIG. 10) wherein a range of stress values is represented along the ordinate of the secondary graph and a range of elongation magnitudes is plotted along the abscissa of the secondary graph. The tensile stress values identified on FIGS. 7-9 for a number of other preselected elongation magnitudes are also added together and the locus of resulting additive values plotted on the secondary graph is the resulting graphical representation which predicts tensile characteristics of the fiber bundle over a broad range of elongation magnitudes.

The information shown in the secondary graph, FIG. 10, may be termed multiple fiber data and as explained above it correlates to some extent with fiber bundle tests, but it is not duplicative of any known bundle test. While the technique of deriving the secondary graph of FIG. 10 has been described with reference to three fibers, in actual practice, many fibers (on the order of 100's) will be tested to provide accurate data as to a particular sample of fibers.

Also, it will be understood that the data shown in FIGS. 7-10 has been chosen to best illustrate the invention and it does not represent any particular fiber sample. It should be noted that the fiber of FIG. 9 elongated for a significant period of time without any tension being produced in the fiber (high crimp) but the fiber of FIG. 8 experienced a tension force immediately upon elongation (low crimp). Usually, elongation of a fiber without placing tension forces on the fiber indicates that the fiber was crimped and the initial elongation is removing crimp. These graphs indicate that the FIG. 9 fiber had a very large amount of crimp, while the FIG. 8 fiber had zero crimp. The differences in the amount of crimp in FIGS. 7-9 help illustrate the invention.

The above described method of obtaining multiple fiber data is not limited to tension and elongation data. For example, in an alternate embodiment, cross sectional data, such as area, diameter or thickness are substituted for elongation and alignment of the data is accomplished according to either time or the cross-sectional data. Also, the multiple fiber data are not limited to two dimensions. For example, one may also produce three coordinate arrays (or three dimensional graphs) using, for example, elongation, tension, and a cross sectional characteristic.

It will be understood that numerous modifications and substitutions can be had to the aforedescribed embodiments without departing from the spirit of the invention. Accordingly, the aforedescribed embodiments are intended for the purpose of illustration and not as limitation.

What is claimed is:

1. An apparatus for testing a single bundle of fibers, comprising:

first and second support members for engaging and holding first and second portions, respectively, of the bundle of fibers;

vacuum means for providing a first suction adjacent to said first support member and a second suction adjacent to said second support member, said first and second support member being disposed between said first and second suctions, said first and second suctions being oppositely oriented to draw the bundle in opposite directions and thereby place the bundle in a substantially linear configuration with portions of the bundle being positioned for engagement by said first and second support members;

translation means for providing relative movement between said support member to tension the bundle between said support members; and monitoring means for monitoring at least one characteristic of the bundle as it is tensioned.

2. The apparatus of claim 1 further comprising:

physical guide means disposed adjacent to said support members for physically engaging the bundle of fibers to facilitate positioning of the bundle for being engaged by said first and second support members.

3. An apparatus for testing a single fiber, said apparatus comprising:

a first support member for engaging and holding a first portion of the fiber;

a second support member for engaging and holding a second portion of the fiber whereby the fiber extends between and is supported by said first and second support members;

positioning means for positioning said fiber adjacent to at least one of said support members in a proper position for being engaged by said at least one support member, whereby said positioning means facilitates the operation of placing a fiber into engagement with said at least one support member;

translation means for providing relative movement between said first and second support member to tension the fiber between said first and second support member;

monitoring means for monitoring at least one characteristic of the fiber as it is tensioned;

said first and second support members comprising first and second clamps, each clamp having engagement surfaces moveable between a first position for clamping and holding the fiber and a second position for releasing the fiber; and said positioning means comprising vacuum means for providing a suction that operates on a fiber positioned between said first and second clamps to move the fiber into position for being clamped by the engagement surfaces of both of said clamps, said vacuum means providing a first suction adjacent to said first clamp and second suction adjacent said second clamp, said first and second suctions being oppositely oriented to draw the fiber in opposite directions and thereby place the fiber in a subsequently linear configuration with the ends of the fiber being positioned for engagement by the engagement surfaces of the first and second clamps.

4. An apparatus for testing a single fiber, said apparatus comprising:

a first support member for engaging and holding a first portion of the fiber;

a second support member for engaging and holding a second portion of the fiber whereby the fiber extends between and is supported by said first and second support members;

positioning means for positioning said fiber adjacent to at least one of said support members in a proper position for being engaged by said at least one support member, whereby said positioning means facilitates the operation of placing a fiber into engagement with said at least one support member;

translations means for providing relative movement between said first and second support members to tension the fiber between said first and second support members;

monitoring means for monitoring at least one characteristic of the fiber as it is tensioned;

at least one of said support members comprising a clamp having engagement surfaces moveable between a first position for clamping and holding the fiber and a second position for releasing the fiber; and said positioning means comprising vacuum means including a vacuum source and a vacuum conduit connected thereto, said vacuum conduit being disposed to one side of said clamp for drawing the fiber into proper position for being engaged by the engagement surfaces of said clamp.

5. The apparatus of claim 4 wherein said positioning means further comprises:

a first alignment rod positioned adjacent said first clamp for engaging and aligning the fiber with the engagement surfaces of the first claim; and a second alignment rod positioned adjacent to said second clamp for engaging and aligning the fiber with the engagement surfaces of said second clamp.

6. The apparatus of claim 4 wherein said monitoring means comprise means for measuring tension on the fiber.

7. The apparatus of claim 4 wherein said monitoring means comprise means for measuring cross-sectional characteristics of the fiber.

8. The apparatus of claim 4 further comprising microenvironment means surrounding said support members to isolate to an extent the environment around a fiber being tested in the apparatus; and test zone environmental control means for supplying a desired atmosphere to said microenvironment.

9. The apparatus of claim 4 wherein at least one of said clamps comprises a pair of jaws having opposing clamping surfaces and adapted to move toward and away from one another to move said clamping surfaces into and out of contact with one another, said clamping surfaces being provided by a relatively non-resilient material so that when said clamping surfaces are clamped on a fiber positioned between the jaws, the fiber is not cut by said jaws and no tension is placed upon the fiber by said clamping means.

10. The apparatus of claim 4 further comprising:

radiating means disposed to one side of the fiber for directing radiation toward the fiber as it is supported on the first and second clamps; and detector means disposed for detecting radiation from the radiating means after the radiation interacts with the fiber to produce a detection signal in response to the detected radiation that corresponds to a cross-sectional characteristic of the fiber.

* * * * *